United States Patent
Kahn et al.

(10) Patent No.: US 9,968,293 B1
(45) Date of Patent: May 15, 2018

(54) DETECTING AND ESTIMATING SLEEP STAGES

(71) Applicant: DP TECHNOLOGIES, INC., Scotts Valley, CA (US)

(72) Inventors: Philippe Kahn, Santa Cruz, CA (US); Arthur Kinsolving, Santa Cruz, CA (US)

(73) Assignee: DP TECHNOLOGIES, INC., Scotts Valley, CA (US)

( * ) Notice: Subject to any disclaimer, the term of this patent is extended or adjusted under 35 U.S.C. 154(b) by 282 days.

(21) Appl. No.: 14/280,548

(22) Filed: May 16, 2014

(51) Int. Cl.
*A61B 5/00* (2006.01)
*A61B 5/11* (2006.01)

(52) U.S. Cl.
CPC .......... *A61B 5/4812* (2013.01); *A61B 5/0022* (2013.01); *A61B 5/11* (2013.01); *A61B 5/681* (2013.01); *A61B 5/7282* (2013.01); *Y10S 128/923* (2013.01)

(58) Field of Classification Search
CPC ............... Y10S 128/905; Y10S 128/92; Y10S 128/923; Y10S 128/924; Y10S 128/925; A61B 5/4806–5/4821
USPC ...... 600/300, 301, 595; 705/2, 3; 340/573.1, 340/575
See application file for complete search history.

(56) References Cited

U.S. PATENT DOCUMENTS

| | | | |
|---|---|---|---|
| 5,047,930 A * | 9/1991 | Martens | A61B 5/0476 128/920 |
| 5,335,657 A | 8/1994 | Terry, Jr. et al. | |
| 5,928,133 A | 7/1999 | Halyak | |
| 6,928,031 B1 | 8/2005 | Kanevsky et al. | |
| 7,914,468 B2 | 3/2011 | Shalon et al. | |
| 8,398,546 B2 | 3/2013 | Pacione et al. | |
| 2002/0080035 A1 | 6/2002 | Youdenko | |

(Continued)

FOREIGN PATENT DOCUMENTS

| | | |
|---|---|---|
| EP | 1139187 B1 | 10/2001 |
| WO | WO 2011/141840 A1 | 11/2011 |

OTHER PUBLICATIONS

Schulz, et al. "Phase shift in the REM sleep rhythm." Pflügers Archiv 358.3 (1975): Abstract.*

(Continued)

*Primary Examiner* — David J McCrosky
(74) *Attorney, Agent, or Firm* — Nicholson De Vos Webster & Elliott LLP

(57) ABSTRACT

Exemplary methods, apparatuses, and systems receive a plurality of user characteristics. The characteristics are transmitted to a server. A sleep profile selected by the server based upon the characteristics is received. The sleep profile includes an estimated sleep cycle having a plurality of stages representing aggregated sleep data from a plurality of persons. The sleep profile is selected in response to determining that the plurality of persons is associated with characteristics similar to the received user characteristics. A shift from a first stage in a current sleep cycle to a second stage in a current sleep cycle is detected. The detection of the shift is based upon a set of data from a sensor measuring physical indications of the user's sleep. An estimate of an additional portion of the current sleep cycle is generated by matching the detected shift to a corresponding shift between stages in the estimated sleep cycle.

21 Claims, 6 Drawing Sheets

(56) References Cited

U.S. PATENT DOCUMENTS

| | | | |
|---|---|---|---|
| 2004/0049132 A1 | 3/2004 | Barron et al. | |
| 2005/0143617 A1 | 6/2005 | Auphan | |
| 2005/0154330 A1 | 7/2005 | Loree, IV | |
| 2005/0190065 A1 | 9/2005 | Ronnholm | |
| 2006/0064037 A1 | 3/2006 | Shalon et al. | |
| 2006/0266356 A1* | 11/2006 | Sotos | A61B 5/4812 128/204.23 |
| 2006/0293602 A1 | 12/2006 | Clark | |
| 2006/0293608 A1 | 12/2006 | Rothman et al. | |
| 2007/0287930 A1 | 12/2007 | Sutton | |
| 2008/0191885 A1 | 8/2008 | Loree, IV et al. | |
| 2008/0234785 A1 | 9/2008 | Nakayama et al. | |
| 2009/0048540 A1 | 2/2009 | Otto et al. | |
| 2009/0082699 A1 | 3/2009 | Bang et al. | |
| 2009/0105785 A1 | 4/2009 | Wei et al. | |
| 2009/0143636 A1 | 6/2009 | Mullen et al. | |
| 2010/0010330 A1 | 1/2010 | Rankers et al. | |
| 2010/0079294 A1 | 4/2010 | Rai et al. | |
| 2010/0100004 A1 | 4/2010 | van Someren | |
| 2010/0217146 A1* | 8/2010 | Osvath | A61B 5/0478 600/544 |
| 2011/0015495 A1 | 1/2011 | Dothie et al. | |
| 2011/0054279 A1* | 3/2011 | Reisfeld | A61B 5/4818 600/323 |
| 2011/0230790 A1 | 9/2011 | Kozlov | |
| 2011/0295083 A1 | 12/2011 | Doelling et al. | |
| 2014/0288878 A1* | 9/2014 | Donaldson | A61B 5/1123 702/141 |
| 2015/0190086 A1* | 7/2015 | Chan | A61B 5/4812 600/301 |

OTHER PUBLICATIONS

Schulz, et al. "The REM-NREM sleep cycle: renewal process or periodically driven process?." Sleep 2.3 (1980): 319-328.*
Estimate. (2011). The American Heritage dictionary of the English language (5th ed.). Boston, MA: Houghton Mifflin. Retrieved from <http://search.credoreference.com/content/entry/hmdictenglang/estimate/0> on Jul. 24, 2017.*
Rechtschaffen et al, "Manual of Standardized Terminology, Techniques and Scoring System for Sleep Stages of Human Subjects." (1968).*
Yassouridis, et al. "Modelling and exploring human sleep with event history analysis." Journal of sleep research 8.1 (1999): 25-36.*
"David F Dinges," <en.wikipedia.org/wiki/David_Dinges>, Last Modified Sep. 12, 2012, 2 pages.
"Fitbit Product Manual," <http://www.fitbit.com/manual>, Last updated Mar. 29, 2010, 20 pages.
"How BodyMedia FIT Works," <http://www.bodymedia.com/Shop/Learn-More/How-it-works>, accessed Jun. 17, 2011, 2 pages.
"Power Nap," <en.wikipedia.org/wiki/Power_nap>, Last Modified Sep. 20, 2012, 4 pages.
"Sara Mednick," <en.wikipedia.org/wiki/Sara_Mednick>, Last Modified Sep. 12, 2012, 2 pages.
"Sleep Debt," <en.wikipedia.org/wiki/Sleep_debt>, Last Modified Aug. 25, 2012, 3 pages.
"Sleep Inertia," <en.wikipedia.org/wiki/Sleep_inertia>, Last Modified Sep. 12, 2012, 2 pages.
"Sleep," <en.wikipedia.org/wiki/Sleep_stages#Physiology>, Last Modified Oct. 5, 2012, 21 pages.
"Slow Wave Sleep," <en.wikipedia.org/wiki/Slow-wave_sleep>, Last Modified Jul. 22, 2012, 4 pages.
Jetlog Reviewers Guide, <http://www.jetlog.com/fileadmin/Presse_us/24x7ReviewersGuide.pdf>, 2009, 5 pages.
Liden, Craig B, et al, "Characterization and Implications of the Sensors Incorporated into the SenseWear™ Armband for Energy Expenditure and Activity Detection," <http://www.bodymedia.com/Professionals/Whitepapers/Characterization-and-Implications-of-the-Sensors-Incorporated-into-the-SenseWear>, accessed Jun. 17, 2011, 7 pages.
PCT Application No. PCT/US2012/46477, Search History, Date of Search Sep. 12, 2012, 3 pages.
PCT/US2012/046477, International Search Report and Written Opinion, dated Sep. 28, 2012, 10 pages.
PowerNap iPhone App, <http://forums.precentral.net/webos-apps-software/223091-my-second-app-powernap-out-app-catalog-nap-timer.html>, Jan. 6, 2010, 10 pages.
Sunseri, Maria, et al, "The SenseWear™ Armband as a Sleep Detection Device," <http://sensewear.bodymedia.com/SenseWear-Studies/SW-Whitepapers/The-SenseWear-armband-as-a-Sleep-Detection-Device>, 2005, 9 pages.
Jaines, Kira, "Music to Help You Fall Sleep," <http://www.livestrong.com/article/119802-music-fall-sleep/>, May 10, 2010, 2 pages.
Leeds, Joshua, "Sound-Remedies.com: Sonic Solutions for Health, Learning & Productivity," <http://www.sound-remedies.com/ammusforslee.html>, Accessed May 23, 2013, 2 pages.
PCT/US2013/028939, International Preliminary Report on Patentability, dated Jan. 23, 2014, 8 pages.
Actigraphy, From Wikipedia, the free encyclopedia, downloaded at: http://en.wikipedia.org/wiki/Actigraphy on Apr. 24, 2014, 4 pages.
Lichstein, et al., Actigraphy Validation with Insomnia, Sleep, vol. 29, No. 2, 2006, pp. 232-239.
Pires, P. D. C. Activity Characterization from Actimetry Sensor Data for Sleep Disorders Diagnosis, Universidade Técnica de Lisboa, Sep. 2008, 60 pages.
Pollak, et al., How Accurately Does Wrist Actigraphy Identify the States of Sleep and Wakefulness?, Actigraphy and Sleep, Sleep, vol. 24, No. 8, 2001, pp. 957-965.
Desai, Rajiv, The Sleep, Archive for Mar. 2011, Dr. Rajiv Desai Blog, Mar. 17, 2011, 46 pages.
Patel, et al., Validation of Basis Science Advanced Sleep Analysis, Estimation of Sleep Stages and Sleep Duration, Basis Science, San Francisco, CA, Jan. 2014, 6 pages.

* cited by examiner

100% of the plurality of persons may be averaged or aggregated in
DETECTING AND ESTIMATING SLEEP STAGES

FIELD OF THE INVENTION

The various embodiments described herein relate to monitoring sleep cycles. In particular, embodiments described herein relate to detecting shifts between sleep stages and estimating additional portions of a corresponding sleep cycle based upon an aggregated sleep profile.

BACKGROUND OF THE INVENTION

A period of sleep includes one or more cycles of different sleep stages that enable a person to recover mentally and physically. For example, rapid eye movement (REM) sleep is associated with strengthening memories, boosting mood, and consolidating information learned during the day. Non-rapid eye movement (NREM) sleep is associated with muscle and tissue recovery, stimulation of physical growth and development, and strengthening of the immune system. By tracking a person's total period of sleep and the corresponding progression through the stages of sleep, a sleep tracking system is able to determine if the person is getting an optimal amount of sleep for mental and/or physical recovery as well as diagnose sleep disorders.

Polysomnography (PSG) is a comprehensive recording of biophysiological changes that occur during sleep. For example, PSG may monitor activity of the brain, eye(s), muscle(s), and heart of a person during sleep. As a result, PSG is able to determine which portions of the person's sleep period are spent in the various stages of sleep. While often considered the "gold standard" of sleep monitoring, PSG may include monitoring a person in a laboratory setting. Such a setting is often expensive and may induce anxiety or otherwise discourage normal sleep period/cycles. Additionally, PSG includes attaching up to 22 electrodes to a person undergoing the sleep monitoring. Given the expensive and invasive nature of PSG, it is not ideal for persons seeking to track sleep on a regular basis in order to optimize sleep and the corresponding physical and mental recovery.

SUMMARY OF THE INVENTION

Exemplary methods, apparatuses, and systems receive a plurality of user characteristics. For example, the user characteristics may include one or more biometric traits of the user, one or more environmental factors prior to or during the current sleep cycle, a time the user begins a period of sleep, food and/or drink the user consumed prior to a time the user begins a period of sleep, and/or an amount of user movement prior to a time the user begins the period of sleep. Exemplary biometric traits include age, sex, height, weight, body mass index (BMI), medical conditions, etc. Exemplary environmental factors include whether the person is sleeping at home or not, temperature, elevation, geographic location, season, hours of sunlight, whether or not the user sleeps in a bed with another person or a pet, etc.

In one embodiment, the characteristics are transmitted to a server. A sleep profile selected by the server based upon the characteristics is received. In another embodiment, a plurality of sleep profiles are stored locally and the sleep profile is selected from one of the plurality of sleep profiles based upon the characteristics. The selected sleep profile includes an estimated sleep cycle having a plurality of stages representing aggregated sleep data from a plurality of persons. For example, the duration of each stage of sleep from each of the plurality of persons may be averaged or aggregated in another manner to produce a duration of an estimated sleep stage that represents the entire plurality. The sleep profile is selected in response to determining that the plurality of persons is associated with characteristics similar to the received user characteristics. For example, sleep data may be aggregated in a sleep profile for all females within a particular age range and BMI range. If the user is a female of an age and BMI that falls into the corresponding ranges, the sleep profile is selected. The estimated sleep cycle of the sleep profile is used to predict one or more subsequent sleep stages for a sleeping user.

A shift from a first stage in a current sleep cycle of the user to a second stage in a current sleep cycle of the user is detected. The detection of the shift is based upon a set of data from a sensor measuring physical movement of and/or one or more biosignals from the user. For example, the user may wear a wristband that includes an accelerometer (e.g., an actigraph or activity tracker) to track user movement. The wristband, or a computing device coupled to the wristband, detects the shift in sleep stages based upon changes in movement type and/or density. In one embodiment, one or more additional or alternative sensors are used to detect shifts between sleep stages. For example, detected movement may be combined with sensor data representing one or more of body temperature, heart rate, blood pressure, breathing patterns, skin conductivity, etc.

An estimate of an additional portion of the current sleep cycle is generated by matching the detected shift to a corresponding shift between stages in the estimated sleep cycle. For example, a graph of the estimated sleep cycle may be used to interpolate the occurrence and duration of one or more stages of the sleep cycle that occur between two detected stages of the current sleep cycle. In one embodiment, the current sleep cycle including the estimated additional portion(s) is displayed or otherwise presented to the user. Additionally, the detected stages of the current sleep cycle may be used to further refine the selected sleep profile.

Other features and advantages will be apparent from the accompanying drawings and from the detailed description.

BRIEF DESCRIPTION OF THE DRAWINGS

The present invention is illustrated by way of example and not limitation in the figures of the accompanying drawings, in which like references indicate similar elements, and in which.

DETAILED DESCRIPTION

Embodiments described herein detect and estimate sleep stages in a sleep cycle. For example, embodiments select a sleep profile based upon received user characteristics. The selected sleep profile includes an estimated sleep cycle having a plurality of stages representing aggregated sleep data from a plurality of persons with characteristics similar to the received user characteristics. Motion detection sensor data representing the user's physical movement is used to detect shifts between stages in a current sleep cycle. Matching the detected shifts to corresponding shifts between stages in the estimated sleep cycle from the selected sleep profile, embodiments generate an estimate of one or more portions of the current sleep cycle in addition to the detected shifts. As a result, embodiments described herein are able to generate a representation of one or more sleep cycles of a user that approaches the accuracy of polysomnography (PSG) without the corresponding expense and invasive nature of PSG.

Figure 1:
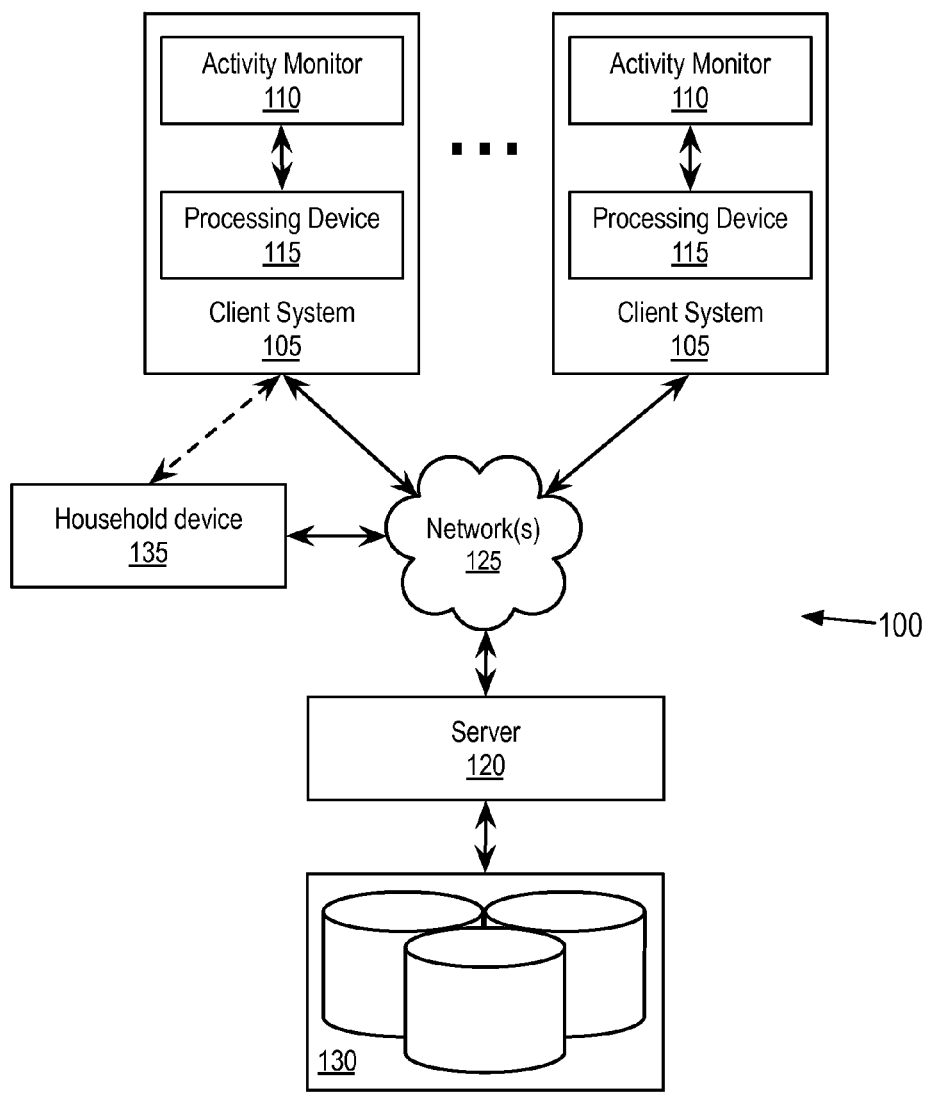
FIG. 1 illustrates, in block diagram form, an exemplary system including one or more networked devices implementing the detection and estimation of sleep stages.

FIG. 1 illustrates, in block diagram form, exemplary system 100 including one or more networked processing devices implementing the detection and estimation of sleep stages. System 100 includes one or more client systems 105. Each client system 105 includes activity monitor 110 and processing device 115. In one embodiment, activity monitor 110 and processing device 115 are embodied within a single device. For example, client system 105 may be an actigraph or other activity-monitoring device including one or more sensors and a processing device to detect shifts between sleep stages and communicate via a wired or wireless connection with server 120. Alternatively, activity monitor 110 and processing device 115 are embodied in separate devices and communicate with one another via a wired or wireless connection. For example, activity monitor 110 may be an actigraph or other activity monitor and communicates via a wired or wireless connection with a phone, tablet, laptop computer, desktop computer, or other personal computing device.

Exemplary activity monitors 110 include one or more inertial sensors, accelerometers, gyroscopes, or a combination thereof (collectively referred to herein as one or more sensors measuring user movement). Additionally, activity monitor 110 may be embodied in a form factor to enable a user to wear, affix, or otherwise incorporate the device to the user's wrist, arm, torso, or other portion of the body or to/within a pillow or mattress. In one embodiment, activity monitor 110 (or client system 105 more generally) includes additional sensors (not shown in FIG. 1). For example, client system 105 may include one or more sensors to track body temperature, heart rate, blood pressure, blood oxygen levels, electrical activity of the heart (electrocardiography), electrical activity of a skeletal muscle (electromyography), acoustic activity (e.g., breathing patterns), skin conductivity (galvanic skin response), and/or another tracked biosignal (collectively referred to herein, along with tracked user movement, as physical indications of sleep from the user). These tracked biosignals may be tracked non-invasively, e.g., via sensor(s) worn against the body rather than connecting probes to a subject's head to measure brainwaves and eye movement. In one embodiment, client system includes two temperature sensors, one to detect the user's body temperature and another to detect ambient temperature.

Activity monitor 110 or processing device 115 utilize measured user movement from the one or more sensors to identify when the user falls asleep or shifts between stages of sleep. For example, the density and/or kind of detected movements are used to differentiate wakefulness, REM sleep, and one or more stages of NREM sleep. In one embodiment, the detected movements are compared to threshold values of movement density, speed, time, distance, etc. and mapped to a corresponding stage of sleep. In one embodiment, client system 105 detects shifts between stages of sleep without additional monitoring of the user. For example, the detection may include measuring user movement using one or more inertial sensors, accelerometers, gyroscopes, or a combination thereof and without monitoring brainwaves, eye movement, or other biophysiological changes. In another embodiment, client system 105 detects shifts between stages of sleep based upon a combination of detected movements and one or more of the non-invasively tracked biosignals described above. For example, during REM sleep, the heart rate and breathing quickens, the blood pressure rises, and body temperature regulation declines while the rest of the body is essentially paralyzed. Client system 105 may use sensor fusion to collect data from multiple sensors to detect an increase in heart rate in conjunction with decrease in physical movement and determine that a shift into REM sleep has occurred.

In one embodiment, activity monitor 110 receives user input (e.g., via a button press, command from processing device 115, etc.) to initiate the monitoring of movements to identify when the user falls asleep or shifts between stages of sleep. As described in greater detail herein, processing device 115 includes an input interface, e.g., to receive commands for activity monitor 110 and data for the creation of a user profile and/or selection of an aggregated sleep profile.

Client system(s) 105 are coupled to server 120 via one or more networks 125 (e.g., a local area network or other private or publically accessible wide area network, such as the Internet). Server 120 is further coupled to storage 130. As described in greater detail herein, server 120 responds to requests for and otherwise maintains aggregated sleep profiles stored within storage 130. For example, client system 105 may transmit one or more user characteristics to server 120. Server 120 retrieves a sleep profile aggregated from users with similar characteristics from storage 130 and returns it to client system 105. Additionally, server 120 may receive user characteristics and sleep data from client system(s) 105 and create or update one or more sleep profiles.

In one embodiment, client system(s) 105 are further coupled, either directly or via network(s) 125, to household device 135. Exemplary household devices 135 include thermostats, lighting systems, and home automation devices/hubs. Household device(s) 135 transmit data to client system(s) 105 indicative of environmental factors that may further characterize a user sleep profile. For example, the household temperature, time lighting was turned on/off, time a television was turned on/off, etc. may affect a user's sleep and used to select a corresponding sleep profile.

Figure 2:
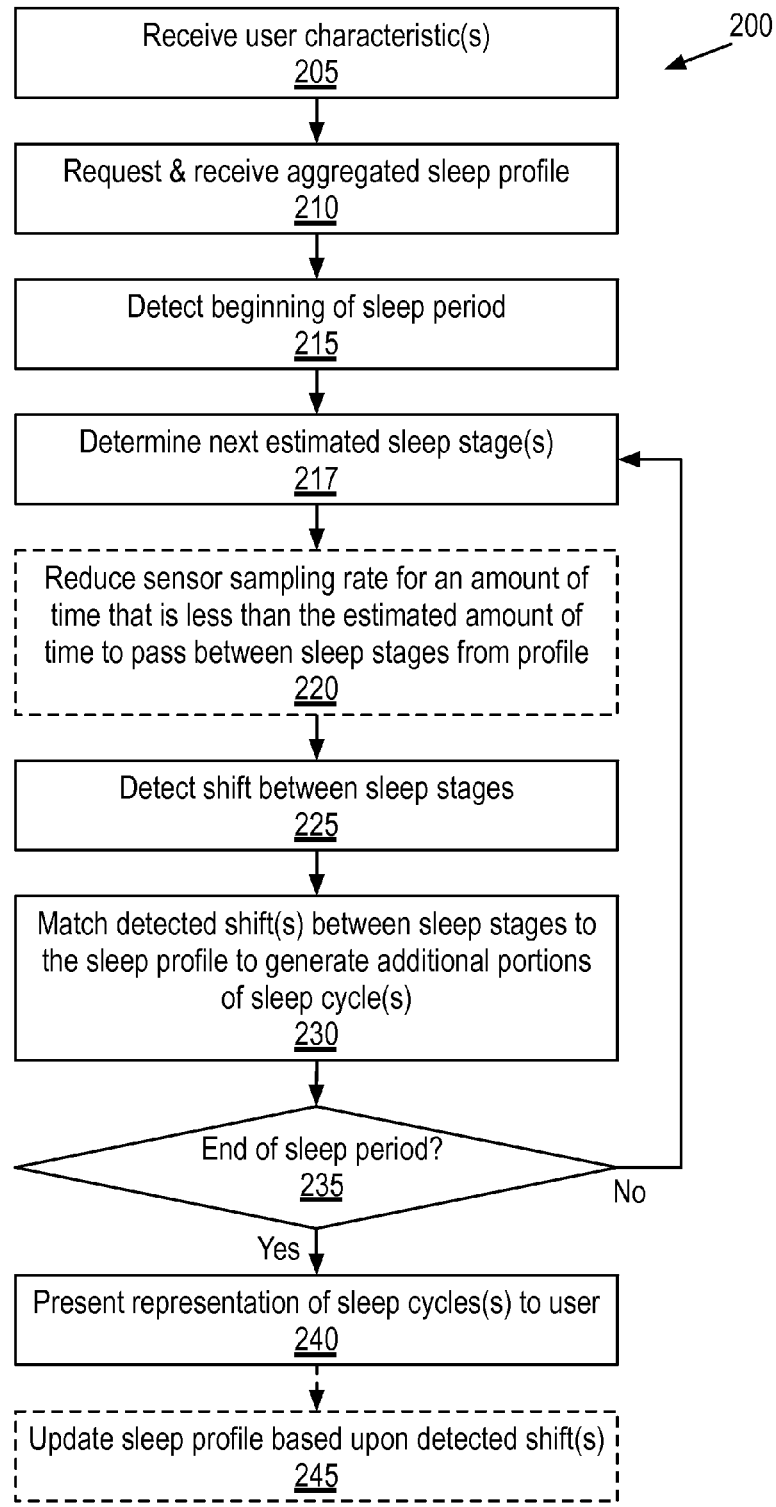
FIG. 2 is a flow chart illustrating an exemplary method of detecting and estimating sleep stages.

FIG. 2 is a flow chart illustrating an exemplary method of detecting and estimating sleep stages. At block 205, client system 105 receives input including one or more user characteristics. For example, the input may include one or more biometric traits of the user. Exemplary biometric traits include age/date of birth, sex, height, weight, body mass index (BMI), medical conditions, etc. In one embodiment, biometric traits are calculated based upon the input. For example, BMI may be calculated using received input of height and weight. Additionally, user characteristics may include one or more environmental factors prior to or during the current sleep cycle. Exemplary environmental factors include a location where the person is sleeping (home, hotel, etc.), temperature, elevation, geographic location, season, hours of sunlight, whether the user sleeps in a bed with another person or a pet, etc. For example, client system 105 determines one or more environmental factors using a current location of client system 105 (e.g., via an internal geolocation positioning system), input from household device 135 (e.g., indicating temperature or lighting conditions), a current date/time maintained or received by client system 105, and/or a look up table or other data structure providing elevation, season, and/or hours of sunlight based upon location and/or date. User characteristics may further include a time the user begins a period of sleep, food and/or drink the user consumed prior to a time the user begins a period of sleep, and/or an amount of user activity prior to a time the user begins the period of sleep. For example, activity monitor 110 may track steps taken by the user throughout the day and/or client system 105 or otherwise directly or indirectly receive input indicating that the user engaged in a physical activity. As another example, client system 105 may receive input indicating an amount of caffeinated beverages consumed by the user at one or more parts of the day.

At block 210, client system 105 transmits a request to server 120 for an aggregated sleep profile that corresponds to the received user characteristic(s). The selected sleep profile includes one or more estimated sleep cycles, each having a plurality of sleep stages representing aggregated sleep data from a plurality of persons. For example, server 120 identifies combinations of persons having one or more similar characteristics and selects those persons for a given sleep profile. The duration of each stage of sleep from each of the plurality of persons may be averaged or aggregated in another manner to produce a duration of the sleep stage that represents the entire plurality. As used herein, the term "similar" with reference to user characteristics includes characteristics that are the same as one another, those that fall within the same defined range of values as one another, and those that are within a threshold distance in values of one another.

In one embodiment, client system 105 transmits the user characteristic(s) to server 120 and receives a corresponding sleep profile in response. For example, server 120 stores a plurality of sleep profiles (e.g., within storage 130) and a mapping of characteristics to the sleep profiles. Server 120 determines which mapped characteristics are similar to the received user characteristics, selects the corresponding sleep profile, and transmits the selected sleep profile to client system 105.

In one embodiment, client system 105 stores a plurality of sleep profiles (e.g., received from server 120) and a mapping of characteristics to the sleep profiles. Client system 105 determines which mapped characteristics are most similar to/within a range of similarity of the received user characteristics and selects the corresponding sleep profile.

In one embodiment, the features of block 205 and/or 210 are not implemented with every execution of method 200. For example, block 205 may be executed as an initial set up of a user account and the data may be used for multiple executions of method 200. Additionally, block 205 may be executed in response to an update of user characteristics.

At block 215, client system 105 detects the beginning of a sleep period for a user. For example, using activity monitor 110, client system 105 determines that the density and/or kind of detected movements correlate to the user transitioning from wakefulness to sleep. As described above, client system 105 may also track one or more biosignals in addition to detecting movement.

At block 217, client system 105 determines the next estimated sleep stage(s). For example, in response to determining that the user has begun a period of sleep or shifted into a particular stage of sleep, client system 105 uses the received sleep profile to predict a duration of time the user will spend in one or more subsequent NREM (N1, N2, and N3) or REM sleep stages of the current sleep cycle. In predicting one or more subsequent sleep stages, client system 105 is able to estimate an amount of time that will pass prior to a time at which or a window of time in which client system 105 is expected to detect a shift between sleep stages.

At block 220, client system 105 optionally reduces the sampling rate of activity monitor 110 in response to detecting the user has begun the sleep period or shifted between sleep stages. A higher sampling rate provides greater accuracy in detecting the density and kind of movements, but uses more battery power than a lower sampling rate. In order to reduce power consumption, client system 105 reduces the sampling rate during periods of time in which the user is estimated to remain in one or more particular stages of sleep. For example, client system 105 may reduce the sampling rate for an amount of time that is less than the estimated duration of a current stage of sleep or otherwise until a window of time in which the shift in sleep stages is predicted to occur, e.g., as indicated by the selected sleep profile.

In one embodiment, client system 105 increases the sampling rate (after the reduction) at a threshold period of time prior to the estimated end of NREM sleep. For example, REM sleep is associated with muscle relaxation/paralysis. A user may be fairly physically active, however, during NREM sleep. As a result, an actigraph or other activity tracker may be more accurate in detecting shifts between REM sleep stages and NREM sleep than between stages within NREM sleep. In such an embodiment, a higher sampling rate is used when REM sleep stages are estimated to occur to track a user's current sleep cycle while a lower sampling rate is used when NREM sleep stages are estimated to occur to reduce power consumption. In an alternate embodiment, client system 105 increases the sampling rate at a threshold period of time prior to the estimated end of a stage within NREM sleep (e.g., the end of the N1 or N2 stage of sleep).

At block 225, client system 105 detects one or more shifts between sleep stages based upon a set of data from a sensor measuring physical indications of sleep from the user. For example, using activity monitor 110, client system 105 determines that the density and/or kind of detected movements correlate to the user transitioning from one stage of sleep to another. In one embodiment, client system 105 detects one or more shifts between sleep stages based upon a combination of detected movements and one or more of the non-invasively tracked biosignals, as described above. In one embodiment, the detected shift is between an NREM sleep stage and an REM sleep stage or between a sleep stage and wakefulness. In another embodiment, the detected shift is between stages of NREM sleep.

At block 230, client system 105 matches the detected shift(s) between sleep stages to corresponding predicted shift(s) based upon the selected sleep profile. For example, client system 105 may determine that a detected shift between NREM and REM sleep stages at a particular time in the current sleep period is within a threshold amount of time from a similar predicted shift between NREM and REM sleep stages from the sleep profile. In one embodiment, client system 105 determines the direction of the shift in sleep stages. For example, client system 105 may determine whether the detected shift is from an NREM sleep stage to an REM sleep stage or from an REM sleep stage to an NREM sleep stage to refine the matching to a corresponding shift in the selected sleep profile.

In one embodiment, when the detected shift between sleep stages is different than the predicted shift by a threshold amount of time, client system 105 stores the difference between the detected shift and corresponding predicted shift and/or increments a count of times the detected shift is different than the predicted shift (e.g., across multiple periods of sleep). For example, as described below, if a predicted shift in sleep stages is incorrect for multiple nights of sleep for the user, client system 105 may update the local copy of the sleep profile and/or transmit sleep data to server 120 to update the sleep profile.

In one embodiment, client system 105 does not detect one or more shifts between sleep stages (e.g., within NREM sleep). Client system 105 uses the sleep cycle from the sleep profile to generate estimates of undetected portions of the user's current sleep cycle. For example, given a match between a detected shift and a predicted shift from the selected profile, client system 105 performs an interpolation, curve fitting, or similar algorithm to estimate the unknown portions of the user's current sleep cycle. The generation of estimated portions of the user's sleep cycle is described further with reference to FIGS. 3-4. In one embodiment, client system 105 detects a shift between sleep stages that occurs in a sleep cycle subsequent to the predicted sleep stage from the user profile. For example, the predicted sleep stage may be an REM sleep stage at the end of a first sleep cycle, but, based upon the amount of time that has elapsed from determining that the user has fallen asleep or entered a previous sleep stage, client system 105 determines that the detected shift matches a predicted shift into the REM sleep stage of the second or other subsequent sleep cycle. Similar to the description above, client system 105 uses the sleep cycles from the sleep profile to generate an estimate of one or more of the undetected sleep stages of the user's first and second sleep cycles.

At block 235, client system 105 determines if the sleep period has ended. If the user remains asleep, method 200 returns to block 217 to determine the next estimated sleep stage(s). For example, client system 105 determines if the user remains asleep or is awake based upon the density and/or kind of detected movements or based upon user input (e.g., turning off a client system alarm, changing modes from sleep to active, etc.).

If the sleep period has ended, at block 240, client system 105 presents a representation of the generated sleep cycle(s) to the user. For example, client system 105 may cause the display of a graph of the user's sleep period including the one or more detected shifts between sleep stages and the estimated portions of the sleep cycle(s) generated using the sleep profile. An exemplary graph of the user's sleep period is described with reference to FIG. 4.

At block 245, client system 105 optionally updates (or causes the update of) the sleep profile. For example, client system 105 may update a local copy of the sleep profile and/or transmit data corresponding to the detected sleep stage shifts to server 120. In one embodiment, client system 105 updates the sleep profile in response to a threshold number of number of times of a detected shift between sleep stages differing from the corresponding predicted shift between sleep stages. In one embodiment, a first threshold number of times of a detected shift between sleep stages differing from the corresponding predicted shift between sleep stages for updating a local copy of the sleep profile differs from a second threshold number of times for transmitting data corresponding to the detected sleep stage shifts to server 120. For example, an individual user's sleep may significantly differ from night to night despite corresponding user characteristics remaining the same. As a result, client system 105 uses the second threshold number to only update the sleep profile with server 120 in response to statistically meaningful occurrences.

In one embodiment, client system 105 transmits the user characteristics, the sleep profile, or an identifier for the sleep profile along with the detected sleep stage shifts to server 120 to enable server 120 to determine which sleep profile is to be updated with the detected sleep stage shifts. Server 120 receives the detected sleep stage shifts and includes them in a recalculation of the aggregated sleep cycle(s) for the corresponding user characteristic grouping. As discussed above, the calculation of aggregated sleep cycle(s) includes determining a duration of each stage of sleep for the sleep profile. The duration of each stage of sleep from each of person (during one or more periods of sleep) may be averaged or aggregated in another manner to produce a corresponding duration of the sleep stage that represents the group of one or more users.

Figure 3:
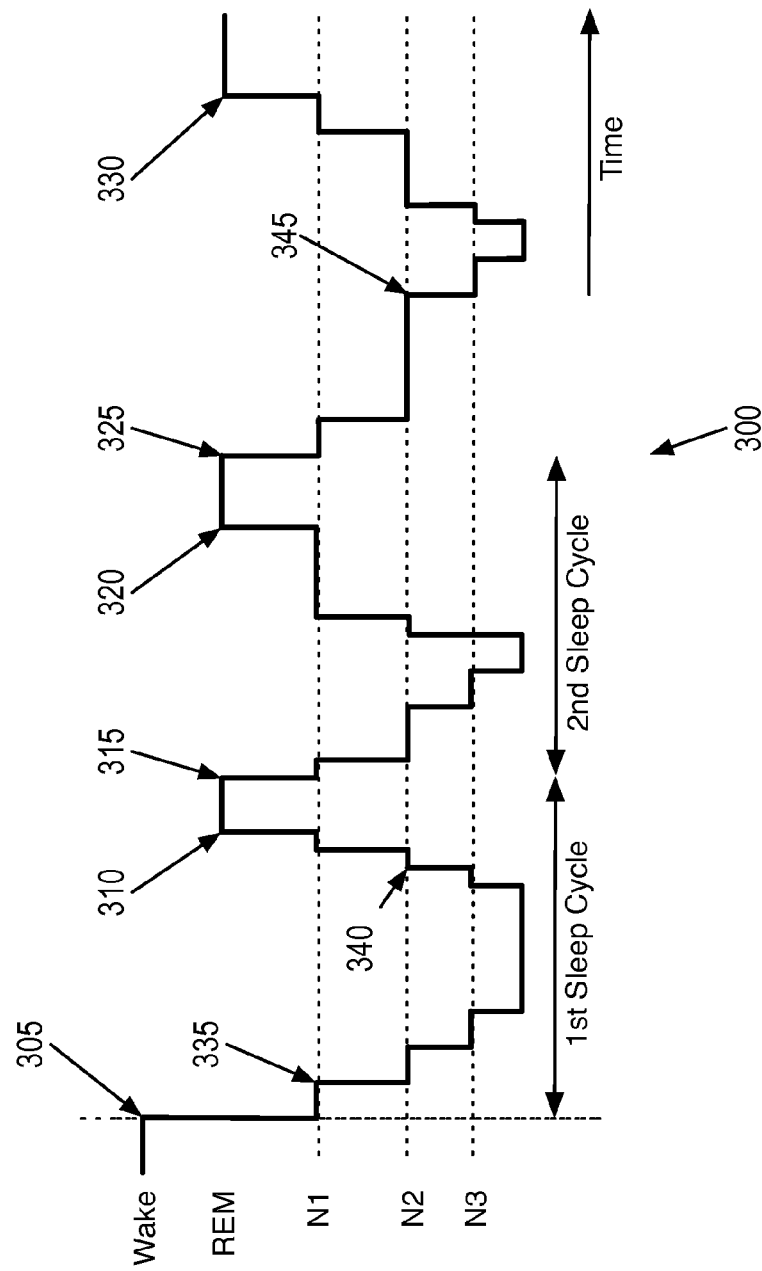
FIG. 3 is a graph that represents an aggregated sleep profile including estimated stages of sleep as a function of time.

FIG. 3 is a graph 300 that represents a sleep profile including estimated stages of sleep that shift as a function of time based upon aggregated sleep data. Graph 300 includes three estimated sleep cycles. A period of sleep, however, may include more or less sleep cycles. As used herein, a sleep cycle refers to a progression through multiple stages of sleep including one or more NREM stages of sleep and an REM stage of sleep. For example, the first sleep cycle includes a portion of sleep between transition 305 from wakefulness to sleep and transition 315 from an REM stage of sleep to an NREM stage of sleep. Similarly, the second sleep cycle includes a portion of sleep between transition 315 from an REM stage of sleep to an NREM stage of sleep and transition 325 from an REM stage of sleep to an NREM stage of sleep.

In one embodiment, graph 300 is created using sleep data aggregated from client systems 105. As described above, client system 105 determines that shifts between stages of sleep have occurred based upon a set of data from one or more sensors measuring physical indications of sleep from the user. For example, indications of sleep may include the density and/or kind of detected movements detected by activity monitor 110 alone or in combination with other non-invasively tracked biosignals. In one embodiment, client system 105 detects shifts between NREM and REM stages of sleep. For example, transitions 310-330 represent detected shifts between NREM and REM stages of sleep. In one embodiment, client system 105 detects shifts between stages within NREM sleep. For example, transitions 335-45 represent detected shifts between stages within NREM sleep. In an alternate embodiment, graph 300 is created using sleep data aggregated from one or more of client systems 105, PSG, and other sleep monitoring systems.

Figure 4:
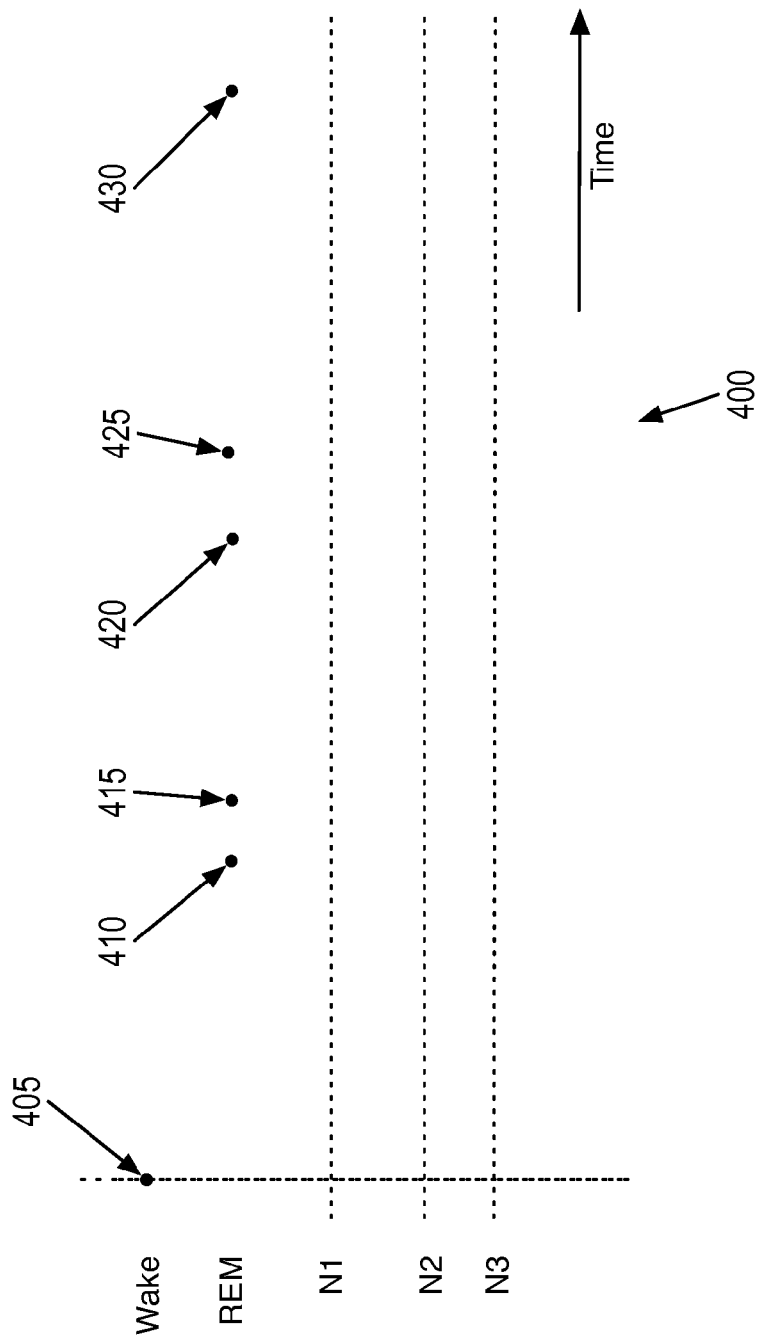
FIG. 4 is a graph of detected shifts in sleep stages in a current period of sleep.

FIG. 4 is a graph 400 of detected shifts in sleep stages in a current period of sleep. As described above, client system 105 determines that shifts between stages of sleep have occurred based upon a set of data from one or more sensors measuring physical indications of sleep from the user. For example, indications of sleep may include the density and/or kind of detected movements detected by activity monitor 110 alone or in combination with other non-invasively tracked biosignals. In the example illustrated by graph 400, client system 105 detected that the user fell asleep at transition 405, entered REM stages of sleep from NREM sleep at transitions 410, 420, and 430, and entered NREM sleep from REM stages of sleep at transitions 415 and 425. In the example illustrated by graph 400, client system 105 did not detect any transitions between stages of NREM sleep. As a result, graph 400 lacks a substantial portion of each sleep cycle. In particular, graph 400 provides no indication of the duration of the individual stages of NREM sleep. In an alternate embodiment, client system 105 detects one or more transitions between stages of NREM sleep but may still lack one or more portions of a given sleep cycle.

Figure 5:
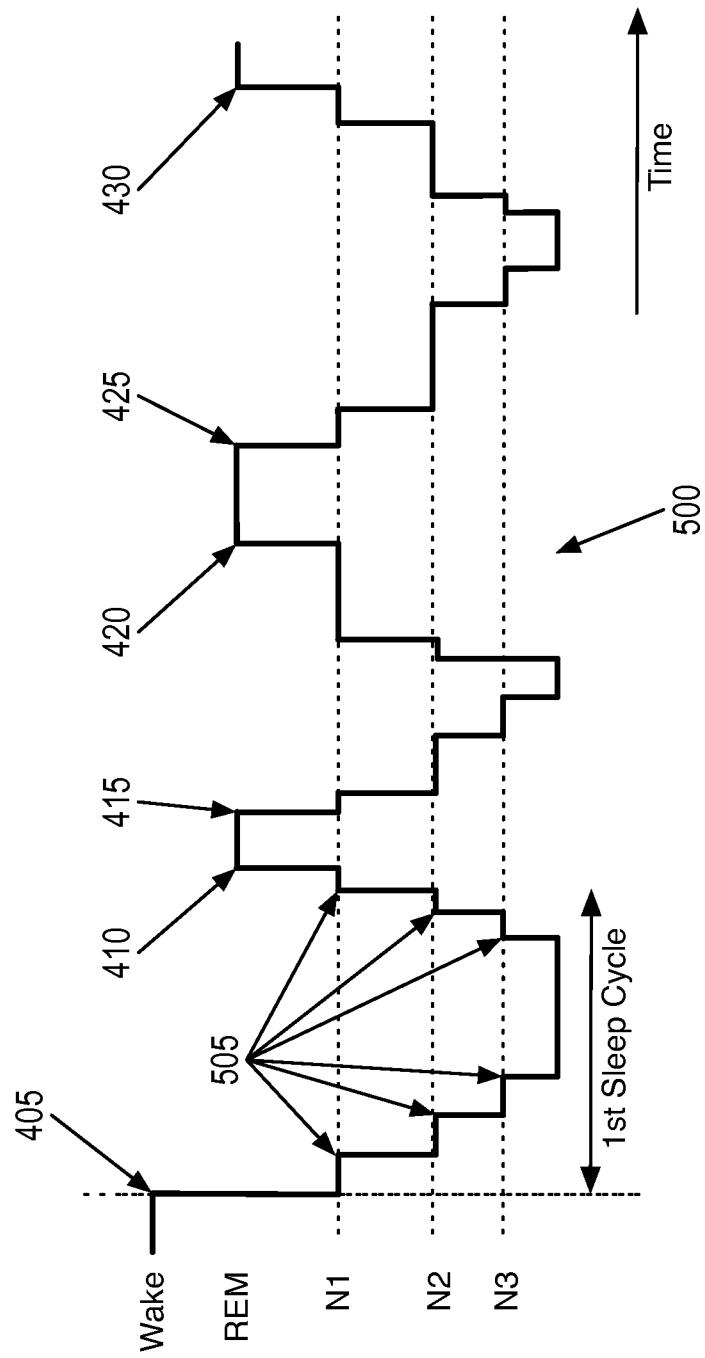
FIG. 5 is a graph of sleep cycles of the current period of sleep including the detected shifts and estimated additional portions of the sleep cycles generated by matching the detected shifts to corresponding shifts between stages in an estimated sleep cycle.

FIG. 5 is a graph 500 of sleep cycles of the current period of sleep including the detected shifts and estimated additional portions of the sleep cycles generated by matching the detected shifts to corresponding shifts between stages in the estimated sleep cycle. As described above, client system 105 uses estimated portions of the sleep cycle from the sleep profile to generate the additional portions of the user's current sleep cycle. For example, given the detected shifts 405-410 and the selected profile (as illustrated by graph 300), client system 105 performs an interpolation, curve fitting, or similar algorithm to estimate additional shifts 505 between stages within the user's current sleep cycle. In one embodiment, if the duration of time between the two detected shifts in the current sleep cycle is greater or less than the duration of time between the corresponding shifts in the sleep profile, client system 105 increases or decreases the duration of time of one or more of the intermediate estimated sleep stages. For example, the duration of time between transition 405 and transition 410 is greater than the duration of time between corresponding transitions 305 and 310. As a result, client system 105 increased the duration of sleep stages N1, N2, and N3 in the estimated first sleep cycle of graph 400. In another embodiment, if the duration of time between the two detected shifts in the current sleep cycle is greater or less than the duration of time between the corresponding shifts in the sleep profile, client system 105 modifies the detected shifts to times closer to the corresponding shifts in the sleep profile.

Figure 6:
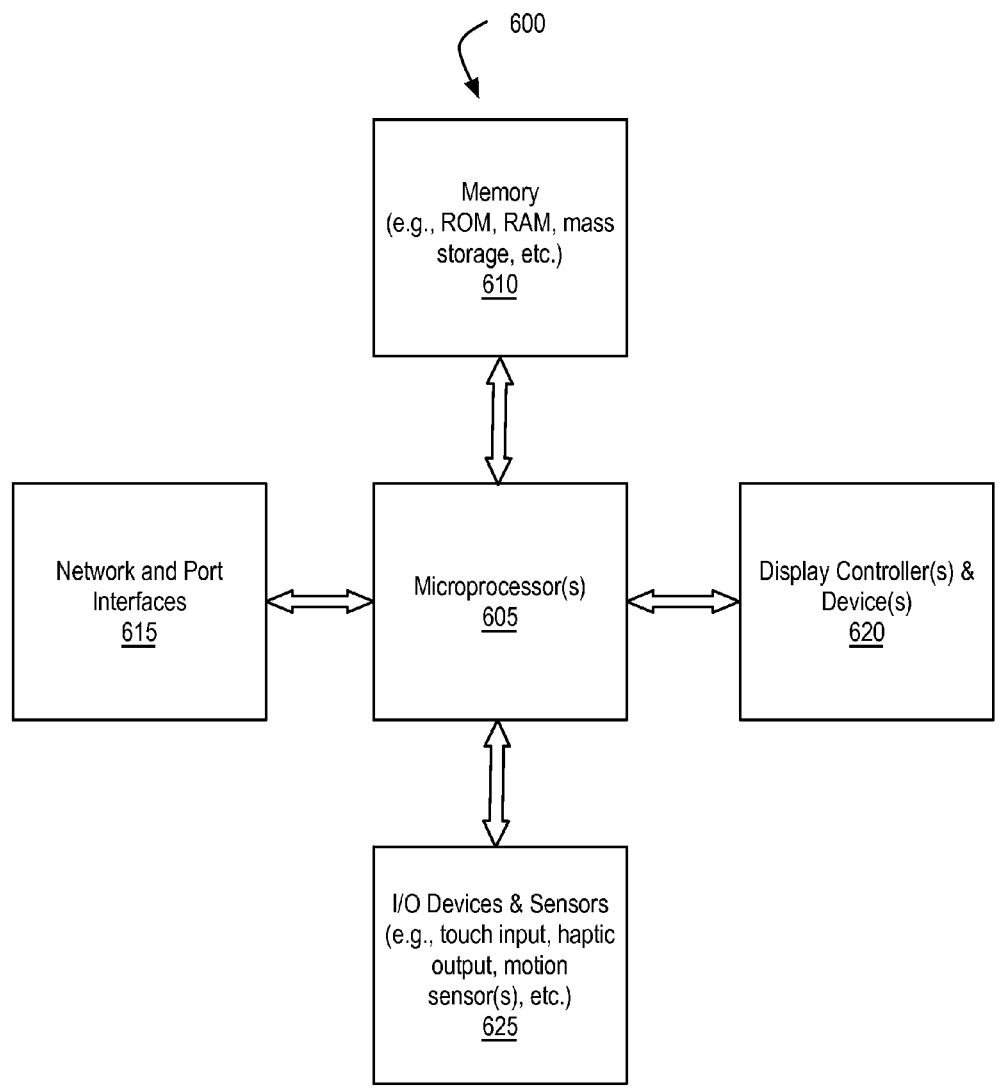
FIG. 6 illustrates, in block diagram form, an exemplary processing system to implement the detection and estimation of sleep stages.

FIG. 6 illustrates, in block diagram form, an exemplary processing system to implement the detection and estimation of sleep stages. Data processing system 600 includes one or more microprocessors 605 and connected system components (e.g., multiple connected chips). Alternatively, data processing system 600 is a system on a chip.

Data processing system 600 includes memory 610, which is coupled to microprocessor(s) 605. Memory 610 may be used for storing data, metadata, and programs for execution by the microprocessor(s) 605. Memory 610 may include one or more of volatile and non-volatile memories, such as Random Access Memory ("RAM"), Read Only Memory ("ROM"), a solid state disk ("SSD"), Flash, Phase Change Memory ("PCM"), or other types of data storage. Memory 610 may be internal or distributed memory.

Data processing system 600 includes network and port interfaces 615, such as a port, connector for a dock, or a connector for a USB interface, FireWire, Thunderbolt, Ethernet, Fibre Channel, etc. to connect the system 600 with another device, external component, or a network. Exemplary network and port interfaces 615 also include wireless transceivers, such as an IS 802.11 transceiver, an infrared transceiver, a Bluetooth transceiver, a wireless cellular telephony transceiver (e.g., 2G, 3G, 4G, etc.), or another wireless protocol to connect data processing system 600 with another device, external component, or a network and receive stored instructions, data, tokens, etc.

Data processing system 600 also includes display controller and display device 620 and one or more input or output ("I/O") devices and sensors 625. For example, data processing system 600 may include one or more touch inputs; buttons; one or more inertial sensors, accelerometers, gyroscopes, or a combination thereof; geolocation positioning systems; vibration motors or other haptic feedback devices; etc. In one embodiment, data processing system 600 includes one or more sensors to track body temperature, heart rate, blood pressure, blood oxygen levels, electrical activity of the heart (electrocardiography), electrical activity of a skeletal muscle (electromyography), acoustic activity (e.g., breathing patterns), skin conductivity (galvanic skin response), and/or another non-invasively tracked biosignal.

Display controller and display device 620 provides a visual user interface for the user. I/O devices 625 allow a user to provide input to, receive output from, and otherwise transfer data to and from the system. I/O devices 625 may include a mouse, keypad or a keyboard, a touch panel or a multi-touch input panel, camera, optical scanner, audio input/output (e.g., microphone and/or a speaker), other known I/O devices or a combination of such I/O devices.

It will be appreciated that one or more buses, may be used to interconnect the various components shown in FIG. 6.

Data processing system 600 is an exemplary representation of one or more of client system(s) 105, activity monitor(s) 110, processing device(s) 115, server 120, storage device(s) 130, and household device(s) 135 described above. Data processing system 600 may be a personal computer, tablet-style device, a personal digital assistant (PDA), a cellular telephone with PDA-like functionality, a Wi-Fi based telephone, a handheld computer which includes a cellular telephone, a media player, an entertainment system, a fitness tracker, or devices which combine aspects or functions of these devices, such as a media player combined with a PDA and a cellular telephone in one device. In other embodiments, data processing system 600 may be a network computer, server, thermostat, home automation hub, or an embedded processing device within another device or consumer electronic product. As used herein, the terms computer, device, system, processing system, processing device, and "apparatus comprising a processing device" may be used interchangeably with data processing system 600 and include the above-listed exemplary embodiments.

It will be appreciated that additional components, not shown, may also be part of data processing system 600, and, in certain embodiments, fewer components than that shown in FIG. 6 may also be used in data processing system 600. It will be apparent from this description that aspects of the inventions may be embodied, at least in part, in software. That is, the computer-implemented method 200 may be carried out in a computer system or other data processing system 600 in response to its processor or processing system 605 executing sequences of instructions contained in a memory, such as memory 610 or other non-transitory machine-readable storage medium. The software may further be transmitted or received over a network (not shown) via network interface device 615. In various embodiments, hardwired circuitry may be used in combination with the software instructions to implement the present embodiments. Thus, the techniques are not limited to any specific combination of hardware circuitry and software, or to any particular source for the instructions executed by data processing system 600.

An article of manufacture may be used to store program code providing at least some of the functionality of the embodiments described above. Additionally, an article of manufacture may be used to store program code created using at least some of the functionality of the embodiments described above. An article of manufacture that stores program code may be embodied as, but is not limited to, one or more memories (e.g., one or more flash memories, random access memories—static, dynamic, or other), optical disks, CD-ROMs, DVD-ROMs, EPROMs, EEPROMs, magnetic or optical cards or other type of non-transitory machine-readable media suitable for storing electronic instructions. Additionally, embodiments of the invention may be implemented in, but not limited to, hardware or firmware utilizing an FPGA, ASIC, a processor, a computer, or a computer system including a network. Modules and components of hardware or software implementations can be divided or combined without significantly altering embodiments of the invention.

In the foregoing specification, the invention has been described with reference to specific exemplary embodiments thereof. Various embodiments and aspects of the invention(s) are described with reference to details discussed herein, and the accompanying drawings illustrate the various embodiments. The description above and drawings are illustrative of the invention and are not to be construed as limiting the invention. References in the specification to "one embodiment," "an embodiment," "an exemplary embodiment," etc., indicate that the embodiment described may include a particular feature, structure, or characteristic, but not every embodiment may necessarily include the particular feature, structure, or characteristic. Moreover, such phrases are not necessarily referring to the same embodiment. Furthermore, when a particular feature, structure, or characteristic is described in connection with an embodiment, such feature, structure, or characteristic may be implemented in connection with other embodiments whether or not explicitly described. Additionally, as used herein, the term "exemplary" refers to embodiments that serve as simply an example or illustration. The use of exemplary should not be construed as an indication of preferred examples. Blocks with dashed borders (e.g., large dashes, small dashes, dot-dash, dots) are used herein to illustrate optional operations that add additional features to embodiments of the invention. However, such notation should not be taken to mean that these are the only options or optional operations, and/or that blocks with solid borders are not optional in certain embodiments of the invention. Numerous specific details are described to provide a thorough understanding of various embodiments of the present invention. However, in certain instances, well-known or conventional details are not described in order to provide a concise discussion of embodiments of the present inventions.

It will be evident that various modifications may be made thereto without departing from the broader spirit and scope of the invention as set forth in the following claims. For example, the methods described herein may be performed with fewer or more features/blocks or the features/blocks may be performed in differing orders. Additionally, the methods described herein may be repeated or performed in parallel with one another or in parallel with different instances of the same or similar methods.

What is claimed is:

1. A computer-implemented method comprising:
   receiving a plurality of user characteristics of a user;
   transmitting the plurality of user characteristics to a server;
   receiving a sleep profile selected by the server based upon the received user characteristics, wherein the selected sleep profile includes an estimated sleep cycle having a plurality of stages generated from aggregated sleep data from a plurality of persons, and wherein the sleep profile is selected in response to determining that the plurality of persons is associated with characteristics similar to the received user characteristics;
   detecting a shift from a first stage in a current sleep cycle of the user to a second stage in a current sleep cycle of the user, the detection of the shift based upon a first set of data from a sensor measuring physical indications of sleep from the user;
   generating a prediction of an additional portion of the current sleep cycle by matching the detected shift to a corresponding shift between stages in the estimated sleep cycle; and
   modifying a sampling rate of the sensor based on the prediction of the additional portion of the current sleep cycle.

2. The computer-implemented method of claim 1, wherein the first stage is a non-rapid eye movement (NREM) stage of sleep and the second stage is a rapid eye movement (REM) stage of sleep.

3. The computer-implemented method of claim 1, wherein the received user characteristics include one or more biometric traits of the user.

4. The computer-implemented method of claim 1, wherein the received user characteristics include one or more environmental factors prior to or during the current sleep cycle.

5. The computer-implemented method of claim 1, wherein the received user characteristics include a time the user begins a period of sleep.

6. The computer-implemented method of claim 1, wherein the received user characteristics include an amount of user activity prior to a time the user begins period of sleep.

7. The computer-implemented method of claim 1, wherein modifying a sampling rate of the sensor based on the prediction of the additional portion of the current sleep cycle further comprises:
   determining that the user has begun a period of sleep based upon a second set of data from the sensor measuring physical indications of sleep from the user;
   reducing the sampling rate of the sensor in response to determining that the user has begun the period of sleep;
   determining, based upon selected sleep profile, an estimated amount of time that will pass between the beginning of the period of sleep and the shift from the first stage in the current sleep cycle to the second stage in a current sleep cycle; and
   increasing the sampling rate prior to passing of the estimated amount of time following the beginning of the period of sleep.

8. The computer-implemented method of claim 1, wherein modifying a sampling rate of the sensor based on the prediction of the additional portion of the current sleep cycle further comprises:
   reducing the sampling rate of the sensor;
   determining, based upon selected sleep profile, an estimated amount of time that will pass between the second stage in the current sleep cycle and a third stage in the current sleep cycle; and
   increasing the sampling rate prior to passing of the estimated amount of time following the detected shift to the second stage.

9. The computer-implemented method of claim 1, wherein the sensor is implemented within a wristband worn by the user during sleep and wherein the indications of sleep include physical motion of a wrist.

10. The computer-implemented method of claim 1, wherein generating the estimate of the additional portion of the current sleep cycle by matching the detected shift to the corresponding shift between stages in the estimated sleep cycle comprises:

determining an amount of time between the detected shift and a detected second shift in the current sleep cycle;

determining a time difference between the determined amount of the time and an estimated amount of time between the corresponding shift and a corresponding second shift in the estimated sleep cycle; and modifying a duration of time of one or more intermediate sleep stages in the estimated sleep cycle based on the determined time difference.

11. A non-transitory computer-readable medium storing instructions, which when executed by a processing device, cause the processing device to perform a method comprising:

receiving a plurality of user characteristics of a user;

transmitting the plurality of user characteristics to a server;

receiving a sleep profile selected by the server based upon the received user characteristics, wherein the selected sleep profile includes an estimated sleep cycle having a plurality of stages generated from aggregated sleep data from a plurality of persons, and wherein the sleep profile is selected in response to determining that the plurality of persons is associated with characteristics similar to the received user characteristics;

detecting a shift from a first stage in a current sleep cycle of the user to a second stage in a current sleep cycle of the user, the detection of the shift based upon a first set of data from a sensor measuring physical indications of sleep from the user;

generating a prediction of an additional portion of the current sleep cycle by matching the detected shift to a corresponding shift between stages in the estimated sleep cycle; and modifying a sampling rate of the sensor based on the prediction of the additional portion of the current sleep cycle.

12. The non-transitory computer-readable medium of claim 11, wherein the first stage is a non-rapid eye movement (NREM) stage of sleep and the second stage is a rapid eye movement (REM) stage of sleep.

13. The non-transitory computer-readable medium of claim 11, wherein the received user characteristics include one or more biometric traits of the user.

14. The non-transitory computer-readable medium of claim 11, wherein the received user characteristics include one or more environmental factors prior to or during the current sleep cycle.

15. The non-transitory computer-readable medium of claim 11, wherein the received user characteristics include a time the user begins a period of sleep.

16. The non-transitory computer-readable medium of claim 11, wherein the received user characteristics include an amount of user activity prior to a time the user begins period of sleep.

17. The non-transitory computer-readable medium of claim 11, wherein modifying a sampling rate of the sensor based on the prediction of the additional portion of the current sleep cycle further comprises:

determining that the user has begun a period of sleep based upon a second set of data from the sensor measuring indications of sleep from movement of the user;

reducing the sampling rate of the sensor in response to determining that the user has begun the period of sleep;

determining, based upon selected sleep profile, an estimated amount of time that will pass between the beginning of the period of sleep and the shift from the first stage in the current sleep cycle to the second stage in a current sleep cycle; and increasing the sampling rate prior to passing of the estimated amount of time following the beginning of the period of sleep.

18. The non-transitory computer-readable medium of claim 11, wherein modifying a sampling rate of the sensor based on the prediction of the additional portion of the current sleep cycle further comprises:

reducing the sampling rate of the sensor;

determining, based upon selected sleep profile, an estimated amount of time that will pass between the second stage in the current sleep cycle and a third stage in the current sleep cycle; and increasing the sampling rate prior to passing of the estimated amount of time following the detected shift to the second stage.

19. The non-transitory computer-readable medium of claim 11, wherein the sensor is implemented within a wristband worn by the user during sleep and wherein the indications of sleep include physical motion of a wrist.

20. An apparatus comprising:

a processing device; and a memory coupled to the processing device, the memory storing instructions which, when executed by the processing device, cause the apparatus to:

receive a plurality of user characteristics of a user;

transmit the plurality of user characteristics to a server;

receive a sleep profile selected by the server based upon the received user characteristics, wherein the selected sleep profile includes an estimated sleep cycle having a plurality of stages generated from aggregated sleep data from a plurality of persons, and wherein the sleep profile is selected in response to determining that the plurality of persons is associated with characteristics similar to the received user characteristics;

detect a shift from a first stage in a current sleep cycle of the user to a second stage in a current sleep cycle of the user, the detection of the shift based upon a first set of data from a sensor measuring physical indications of sleep from the user;

generate a prediction of an additional portion of the current sleep cycle by matching the detected shift to a corresponding shift between stages in the estimated sleep cycle; and modify a sampling rate of the sensor based on the prediction of the additional portion of the current sleep cycle.

21. The apparatus of claim 20, wherein the first stage is a non-rapid eye movement (NREM) stage of sleep and the second stage is a rapid eye movement (REM) stage of sleep.

* * * * *